(12) United States Patent
Lord et al.

(10) Patent No.: US 6,827,929 B1
(45) Date of Patent: Dec. 7, 2004

(54) SCAR TREATMENT COMPOSITION

(75) Inventors: Gary Lord, Lasne (BE); Marie Therese Valencia, Pegomas (FR); Xavier Thomas, Foix (FR)

(73) Assignee: Dow Corning France S.A., Valbonne (FR)

( * ) Notice: Subject to any disclaimer, the term of this patent is extended or adjusted under 35 U.S.C. 154(b) by 177 days.

(21) Appl. No.: 10/070,005

(22) PCT Filed: Sep. 12, 2000

(86) PCT No.: PCT/GB00/03507

§ 371 (c)(1),
(2), (4) Date: Jul. 2, 2002

(87) PCT Pub. No.: WO01/22923

PCT Pub. Date: Apr. 5, 2001

(30) Foreign Application Priority Data

Sep. 27, 1999 (EP) .......................... 99402355

(51) Int. Cl.$^7$ .............................. A61K 31/74
(52) U.S. Cl. ................ 424/78.06; 424/78.08; 427/387

(58) Field of Search ............... 424/400, 78.06, 424/78.08, 401, 78.03

(56) References Cited

U.S. PATENT DOCUMENTS

| 5,496,544 A | 3/1996 | Mellul et al. ............ 424/78.03 |
| 5,567,426 A | 10/1996 | Nadaud et al. ............ 424/401 |
| 5,902,592 A | 5/1999 | Bara et al. ................. 424/401 |

FOREIGN PATENT DOCUMENTS

| EP | 0 300 620 | 6/1988 |
| WO | WO 97/17058 | 5/1997 |
| WO | WO 98/22084 | 5/1998 |

Primary Examiner—Jyothsan Venkat
(74) Attorney, Agent, or Firm—Jim L. De Cesare

(57) ABSTRACT

A composition comprising 1–25 wt. % of a silicone gum, 1–40 wt. % of a silicone fluid having a viscosity of 10 to 60,000 mm$^2$/sec, 1–35 wt. % of a silicone wax and 20–90 wt. % of a volatile silicone fluid having a viscosity up to and including 5 mm$^2$/s at 25° C. can be used for the treatment of scars resulting from injury or surgery.

7 Claims, No Drawings

SCAR TREATMENT COMPOSITION

The present invention relates to a novel composition comprising a silicone fluid, a silicone gum, a silicone wax and a volatile silicone. This composition can be used for the treatment of scars resulting from injury or surgery.

Scars resulting from injury or surgery are undesirable both cosmetically and functionally. Cosmetically, scar tissue is often viewed as unsightly. Functionally, scar tissue often lacks features of undamaged skin such as a normal sense of touch and complete skin integrity.

Numerous methods have been developed to treat and/or prevent scars including surgical treatment, aftercare coverings, pressure treatment, oils, creams, greases, wound dressings such as hydrogel or silicone gels, collagen implantation and laser ablation. For instance, U.S. Pat. No. 4,991,574 teaches a surgical dressing comprising a sheet of silicone gel having a wound-facing surface and, laminated to the other surface, a film of silicone elastomer. This dressing, however, is cumbersome for patients to apply and is difficult to adhere and maintain adherence on certain parts of the body.

Likewise, U.S. Pat. No. 5,741,509 teaches a wound dressing comprising a blend of silicone fluid, fumed silica and a volatile diluent. This patent teaches that the volatile diluent reduces the consistency of the composition so that it can be applied to a wound without producing injury or discomfort. When the volatile diluent evaporates, a stiff cream having increased wound adhesion is left. This material, however, is tacky and fails to provide sufficient occlusivity.

Therefore, one of the objects of the present invention is to provide a scar treatment composition that forms films on the skin which are substantive, semi-occlusive, non-tacky, cosmetically acceptable and easy to apply and remove.

We have now discovered that these properties are delivered by a composition comprising 1–25 wt. % of a silicone gum, 1–40 wt. % of a silicone fluid having a viscosity of 10 to 60,000 $mm^2/s$, 1–35 wt. % of a silicone wax and 20–90 wt. % of a volatile silicone fluid having a viscosity up to and including 5 $mm^2/S$.

These compositions can be used for the treatment of scars resulting from injury or surgery.

The compositions of the present invention have numerous properties which render them useful for forming films on the skin. These include, for example, the films are substantive such that they do not smear, transfer to clothing or exhibit cold flow. Similarly, the films are semi-occlusive such that they provide an emollient and moisturizing effect. Additionally, the compositions are aesthetically pleasant in that they are not tacky (i.e., they have a silky feel), they have a matte appearance (i.e., not shiny), they are comfortable when applied, and they are easy to apply and remove.

Of particular significance is the fact that the compositions of the present invention can be produced in any form from a liquid to a thick paste and, thus, can be delivered by any conventional means.

The first ingredient of the compositions of the invention are silicone gums. These gums provide the compositions herein with the ability to form substantive, matte films and, conversely, without such gums the compositions of the invention are sticky and easily removed (e.g., washing or smearing). While such gums are typically high molecular weight polydimethylsiloxanes terminated with unreactive groups such as trimethylsiloxy or reactive groups such as dimethylhydroxysiloxy or dimethylvinylsiloxy, nearly any silicone gum, or mixtures thereof, will function herein. Most preferably, the silicone gum is a dimethylhydroxysiloxy-terminated polydimethylsiloxane.

Silicone gums typically have viscosities up to 50 million $mm^2/s$ at 25° C. and have number average molecular weights (Mn) of up to 700,000 or more. Preferably, the gums have an Mn of about 200,000 to 400,000.

Such gums and methods for their production are known in the art as exemplified by Noll, Chemistry and Technology of Silicones, Academic Press, 1968. In addition, silicone gums are commercially available from, for example, Dow Corning Corporation.

Generally, silicone gums are added to the composition of the invention in amounts of about 1 to 25 wt %. Preferably, silicone gums are used in an amount of about 5 to 15 wt %.

The composition of the invention also contains silicone fluids having viscosities of about 10 to 60,000 $mm^2/s$ at 25° C. These fluids plasticize the compositions herein and improve their spreadability and conformability. While such fluids are typically linear polydimethylsiloxanes terminated with unreactive groups such as trimethylsiloxy or reactive groups such as dimethylhydroxysiloxy or dimethylvinylsiloxy, nearly any silicone fluid, or mixtures thereof, will function herein. This includes, for example, fluids with small amounts of branching or fluids with organic groups other than methyl attached to silicon.

As noted, the silicone fluids herein will have viscosities of about 10 to 60,000 $mm^2/s$ at 25° C. Preferably, the silicone fluids will have viscosities of about 20 to 20,000 $mm^2/s$ at 25° C. Most preferably, the silicone fluid comprises a mixture of silicone fluids having viscosities of about 20 and about 12,500 $mm^2/s$ at 25° C.

Such fluids and methods for their production are known in the art as exemplified by Noll, Chemistry and Technology of Silicones, Academic Press, 1968. In addition, silicone fluids are commercially available from, for example, Dow Corning Corporation.

Generally, silicone fluids are added to the composition of the invention in amounts of about 1 to 40 wt %. Preferably, silicone fluids are used in an amount of about 20 to 30 wt %.

The composition of the invention also contains silicone waxes. These waxes provide the compositions herein with their silky, non-tacky and semi-occlusive properties. The occlusive property, in turn, provides skin hydration which is a major factor in scar treatment. These waxes also act as a hardening lubricant which causes a reduction in the elastic contribution of the gums under stress and a reduction in the creep of the film. Nearly any silicone wax, or mixtures thereof, will function herein.

Preferred silicone waxes suitable for use in the present invention include alkylmethylsiloxane copolymers having the following formulations:

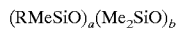    1 or

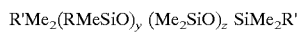    2 wherein R is $C_nH_{2n+1}$, R' is R or Me, Me is $CH_3$, n is 5 to 45, preferably 10–30, a is an integer from 3 to 10, b is an integer of 0 to 10, a+b is 3 to 10 and y and z are independently 0 or a positive integer of, for example, 1–1000, provided the resultant material is waxy in character, i.e., when R' is Me, y must be 1 or greater.

Preferably, the silicone wax comprises a trimethylsiloxy-terminated poly(dimethyl, methyloctadecyl)siloxane.

The silicone waxes of the present invention typically have melting points of between about 30° C. and about 100° C.

Methods for the preparation of such materials are known in the art, and such methods are described in, for example, U.S. Pat. No. 5,017,221 which issued May 21, 1991, and U.S. Pat. No. 5,160,494 which issued Nov. 3, 1992, both of which are incorporated herein by reference. Basically, such methods involve the reaction of a linear siloxane having SiH functionality in the chain with a cyclic siloxane containing $Me_2SiO$ units, and contacting the reaction product with a slight stoichiometric excess of an alkene in the presence of a platinum on carbon catalyst. In addition, silicone waxes are commercially available from, for example, Dow Corning Corporation.

Generally, silicone waxes are added to the composition of the invention in amounts of about 1 to 35 wt %. Preferably, silicone waxes are used in an amount of about 5 to 15 wt %.

The compositions of the invention also contain volatile silicone fluids having viscosities of up to and including about 5 mm$^2$/s. This volatile fluid allows for easy blending and application of the composition to form a thin film without a cold flow effect. While such fluids are typically cyclic or linear polydimethylsiloxanes or permethylsilanes, nearly any volatile silicone fluid, silane, or mixtures thereof, will function herein.

As noted, the volatile silicone fluids generally have a viscosity of up to and including about 5 mm$^2$/s, preferably up to about 1.5 mm$^2$/s at 25° C. and more preferably up to about 1.0 mm$^2$/s at 25° C. such that they volatilize in the ambient environment. Generally, such volatile silicone fluids correspond to the average unit formula $(CH_3)_aSiO_{(4-a)/2}$ where a has an average value of from 2 to 3. Such fluids often comprise siloxane units joined by Si—O—Si bonds selected from the group consisting of $(CH_3)_3SiO_{1/2}$ and $(CH_3)_2SiO_{2/2}$ units taken in such molar amounts so that there is an average of from approximately two to three methyl groups per silicon in the fluid.

The volatile silicone fluids of the invention can also be a permethylsilane corresponding to the average unit formula $(CH_3)_aSi$ where a has an average value of from 2 to 3. Such fluids comprises silane units joined by Si—Si bonds selected from the group consisting of $(CH_3)_3Si$ and $(CH_3)_2Si$ units taken in such molar amounts so that there is an average of from approximately two to three methyl groups per silicon in the fluid.

Preferably the silicone fluid consists essentially of dimethylsiloxane units, and optionally, trimethylsiloxane units. Of particular interest in the present invention are methylsiloxane fluids such as the cyclopolysiloxanes of the general formula $\{(CH_3)_2SiO\}_x$ and linear siloxanes of the general formula $(CH_3)_3SiO\{(CH_3)_2SiO\}_ySi(CH_3)_3$ wherein x is an integer of from 4 to 6 and y is an integer of from 0 to 4.

Preferred silicone fluids or blends of silicone fluids include cyclic silicones such as hexamethylcyclotrisiloxane, octamethylcyclotetrasiloxane, decamethylcyclopentasiloxane, and the like and linear silicones such as hexamethyldisiloxane, octamethyltrisiloxane, decamethyltetrasiloxane, and the like. The preferred volatile silicone fluid is hexamethyldisiloxane.

These volatile silicone fluids and methods for their manufacture are known in the art as exemplified by Noll, Chemistry and Technology of Silicones, Academic Press, 1968. In addition, these volatile silicone fluids are commercially available from, for example, Dow Corning Corporation.

Generally, the volatile silicone fluids are added to the composition of the invention in amounts of about 1 to 90 wt %, preferably 20 to 90 wt % and more preferably 40 to 70 wt %.

The compositions of the present invention may be prepared by simply mixing the components in any desired order. Apparatuses such as stirrers, blenders, mills and the like, and any other means known in the art can be used. In addition pressure vessels, condensing systems and other means known in the art and commonly used to retain a volatile component in a mixture may be employed in the preparation of the present invention.

By changing the ratio of components in the compositions of the present invention, one has great flexibility in producing compositions with a wide range of physical properties and, thus, a wide range of utilities. For example, compositions from liquids to pastes can be produced and these compositions can be changed to suit the type of scar. Similarly, the compositions may be changed for uses outside scar treatment such as in cosmetics, skin care, pharmaceutical delivery, veterinary applications and the like.

The composition of the invention can optionally comprise other ingredients such as additional diluents, dispersants or carriers, emollients, humectants, thickeners, fillers, preservatives, stabilizers, buffer systems, plant extracts, amino acids, activity enhancers, cosmetic ingredients such as colorants, perfumes, emulsifiers, and sunscreens, essential oils, antiparasitics, repellents and pharmaceutical agents.

The following non-limiting examples are provided so that one skilled in the art can more readily understand the invention.

EXAMPLE 1

The present example shows the moisture vapor transmission rate for compositions of the present invention and comparative materials.

Composition A was prepared by thoroughly mixing 26.38 g of dimethylhydroxysiloxy-terminated polydimethylsiloxane gum having an Mn of about 300,000; 18.67 g of trimethylsiloxy-terminated polydimethylsiloxane fluid having a viscosity of 12,500 mm$^2$/s; 37.04 g of trimethylsiloxy-terminated polydimethylsiloxane fluid having a viscosity of 20 mm$^2$/s and 17.9 g of trimethylsiloxy-terminated poly (dimethyl, methyloctadecyl)siloxane wax having a melting point of 32° C. 43 g of composition A was dispersed into 57 g of hexamethyldisiloxane.

Composition B was prepared by thoroughly mixing 26.2 g of dimethylhydroxysiloxy-terminated polydimethylsiloxane gum having an Mn of about 300,000; 19.2 g of trimethylsiloxy-terminated polydimethylsiloxane fluid having a viscosity of 12,500 mm$^2$/s; 36.8 g of trimethylsiloxy-terminated polydimethylsiloxane fluid having a viscosity of 20 mm$^2$/s and 17.8 g of trimethylsiloxy-terminated poly (dimethyl, methyloctadecyl)siloxane wax having a melting point of 32° C. 43 g of composition B was dispersed into 57 g of hexamethyldisiloxane.

A comparative composition C was prepared by thoroughly mixing 26.2 g of dimethylhydroxysiloxy-terminated polydimethylsiloxane gum having an Mn of about 300,000; 19.2 g of trimethylsiloxy-terminated polydimethylsiloxane fluid having a viscosity of 12,500 mm$^2$/s and 36.8 g of trimethylsiloxy-terminated polydimethylsiloxane fluid having a viscosity of 20 mm$^2$/S 43 g of composition C was dispersed into 57 g of hexamethyldisiloxane.

A second comparative composition D comprising lot 1128/107 of the commercial gel Kelocote™ from Allied Biomedical, Paso Robles, Calif.

Each of these materials, compositions A, B, C and D, were tested for moisture vapor transmission rate. The experiment was based on the ASTM E96-95 entitled "Standard Test Methods for Water Transmission of Materials" and conducted according to the following parameters: 1) About 14.5 mg/cm² of tested material was coated with a handcoater onto a 55 mm diameter disc made from a microporous membrane which supports the material during the test. The microporous membrane is a PET membrane with an average pore size of 0.2 μm from 3M™ referenced as 3M™ CoTran 9711 Membrane. 2) Each coated disc was put onto a cylindrical cup (h # 40 mm, Ø # 40 mm) which contains 20 ml of demineralised water. 3) The trials were done in a climatic system at a temperature of 32° C. and at 50% relative humidity. The results are shown in Table 1.

TABLE 1

| Composition | Coated weight (mg/cm²) | MVTR (g/m² · 24 h) |
|---|---|---|
| A | 14.9 | 112.4 |
| B | 14.1 | 109.4 |
| C | 13.5 | 183.5 |
| D | 15.9 | 175.5 |
| blank (membrane CoTran) | 0 | 2625.7 |

MVTR = Moisture Vapor Transmission Rate

EXAMPLE 2

The present example shows the oxygen permeability for materials of the present invention and comparative materials.

Composition A and comparative compositions C and D were prepared as in Example 1.

Each of these materials was tested for oxygen permeability. The experiment was based on a chromatographic method as documented in the ISO/CD 15105-2 and conducted according to the following parameters: 1) About 17.2 mg/cm² of tested material was coated with a handcoater onto a 55 mm diameter disc made from a microporous membrane which supports the material during the test. The microporous membrane is a PET membrane with an average pore size of 0.2 μm from 3M™ referenced as ₃M™ CoTran 9711 Membrane. 2) Each coated disc was put into the chromatography cell to form a 0.5 cm² interface between a flow of helium as chromatographic carrier gas and a flow of gas at atmospheric pressure containing 50% oxygen. 3) The trials were done at a temperature of 23° C. and at 0% relative humidity. The results are shown in Table 2.

TABLE 2

| Composition | Coated weight (mg/cm²) | Oxygen gas permeability (cm³/m² · 24 h · bar) |
|---|---|---|
| A | 15.4 | 52,000 |
| C | 19.5 | 201,600 |
| D | 16.8 | 201,600 |
| blank (membrane CoTran) based on standard NF Q 03076 | 0 | around $10^{10}$ |

EXAMPLE 3

The present example shows the rheological behaviour for materials of the present invention and comparative materials.

Composition A was made by the process described in Example 1.

Comparative composition E was prepared by thoroughly mixing 262.1 g of dimethylhydroxysiloxy-terminated polydimethylsiloxane gum having an Mn of about 300,000; 192 g of trimethylsiloxy-terminated polydimethylsiloxane fluid having a viscosity of 12,500 mm²/s and 368 g of trimethylsiloxy-terminated polydimethylsiloxane fluid having a viscosity of 20 mm²/s. 43 g of composition E was dispersed into 57 g of hexamethyldisiloxane. A second comparative composition F comprises only dimethylhydroxysiloxy-terminated polydimethylsiloxane gum having an Mn of about 300,000.

Each of these materials was tested for its rheological behaviour. The experiment was conducted by recording the elastic and loss moduli of a 0.5 ml sample with a controlled stress rheometer (Carrimed™ CSL 500 from TA Instrument) equipped with a two-parallel plate geometry spaced from 100 μm and the upper plate has a 2 cm diameter. The test conditions were $1.75*10^{-2}$ rad strain for 2 hours under 1 Hz at 25° C. The results are shown in Table 3.

TABLE 3

| Composition | G' (Pa) | G" (Pa) |
|---|---|---|
| A | 1,700 | 1,400 |
| E | 2,400 | 1,200 |
| F | 22,200 | 26,400 |

What is claimed is:

1. A composition consisting of:

1–25 wt. % of a silicone gum;

1–40 wt. % of a silicone fluid having a viscosity of 10 to 60,000 mm²/s at 25° C.;

1–35 wt. % of a silicone wax;

20–90 wt. % of a volatile silicone fluid having a viscosity up to and including 5 mm²/s at 25° C.

2. A method of forming a film on a substrate comprising:

(A) mixing components consisting of:

1–25 wt. % of a silicone gum;

1–40 wt. % of a silicone fluid having a viscosity of 10 to 60,000 mm²/s at 25° C.;

1–35 wt. % of a silicone wax;

20–90 wt. % of a volatile silicone fluid having a viscosity up to and including 5 mm²/s at 25° C.;

(B) applying the mixture formed in (A) to a substrate; and (C) allowing the volatile silicone fluid to evaporate and thereby deposit a film on the substrate.

3. The composition according to claim 1 wherein the silicone gum comprises a hydroxyl-terminated polydimethylsiloxane and is present in an amount of 5 to 15 wt %.

4. The composition according to claim 1 wherein the silicone fluid has a viscosity of 20 to 20,000 mm²/s at 25° C. and is present in an amount of 20–30 wt %.

5. The composition according to claim 4 wherein the silicone fluid comprises a mixture of silicone fluids having a viscosity of about 20 mm²/s at 25° C. and 12,500 mm²/s at 25° C.

6. The composition according to claim 1 wherein the silicone wax comprises a trimethylsiloxy-terminated dimethyl, methyloctadecylsiloxane and is present in an amount of 5 to 15 wt %.

7. The composition according to claim 1 wherein the volatile silicone fluid comprises hexamethyldisiloxane and is present in an amount of 40 to 70 wt %.

* * * * *